United States Patent
Marchand

(10) Patent No.: US 8,298,399 B2
(45) Date of Patent: Oct. 30, 2012

(54) METHOD, DEVICE AND SYSTEM FOR THE MICROANALYSIS OF IONS

(75) Inventor: Gilles Marchand, Pierre Chatel (FR)

(73) Assignee: Commissariat a l'Energie Atomique, Paris (FR)

( * ) Notice: Subject to any disclaimer, the term of this patent is extended or adjusted under 35 U.S.C. 154(b) by 1002 days.

(21) Appl. No.: 12/302,947

(22) PCT Filed: May 24, 2007

(86) PCT No.: PCT/FR2007/000874
§ 371 (c)(1),
(2), (4) Date: Dec. 1, 2008

(87) PCT Pub. No.: WO2007/138180
PCT Pub. Date: Dec. 6, 2007

(65) Prior Publication Data
US 2009/0255830 A1    Oct. 15, 2009

(30) Foreign Application Priority Data
May 31, 2006  (FR) ..................... 06 04865

(51) Int. Cl.
*G01N 27/49* (2006.01)
(52) U.S. Cl. ..... 205/789; 205/702; 205/704; 205/789.5; 422/502
(58) Field of Classification Search .......... 422/502–508; 204/403.01–403.15; 205/702, 704, 775–794.5
See application file for complete search history.

(56) References Cited

U.S. PATENT DOCUMENTS 5,429,734 A * 7/1995 Gajar et al. .................. 204/603
6,630,359 B1 10/2003 Caillat et al.
7,666,285 B1 * 2/2010 Cho et al. ................ 204/403.01
2004/0229222 A1 * 11/2004 Chui et al. ........................ 435/6
(Continued)

FOREIGN PATENT DOCUMENTS
JP    2002-522749    7/2002
(Continued)

OTHER PUBLICATIONS

Visser et al. "Characterization of Hydrophilic and Hydrophobic Ionic Liquids: Alternatives to Volatile Organic Compounds for Liquid-Liquid Separations" In Ionic liquids; Rogers, R., et al. Pub Jul. 25, 2002 pp. 289-307.*

(Continued)

*Primary Examiner* — Kaj K Olsen
*Assistant Examiner* — Susan D Leong
(74) *Attorney, Agent, or Firm* — Oblon, Spivak, McClelland, Maier & Neustadt, L.L.P.

(57) ABSTRACT

A method of microanalyzing ions, which includes: placing in a cavity having an internal volume, a volume of an ionic liquid that is smaller than the internal volume; placing in the cavity a solution containing the ions that are to be analyzed, a solvent of the solution and the ionic liquid being selected so as to be immiscible and so as to enable the ions to be transferred from the solution to the ionic liquid; and detecting a presence of the ions in the ionic liquid with an analyzer that analyzes at least one of cations or anions of the ions in the ionic liquid, in a free state or in a complexed state, the analyzer being in contact with the ionic liquid.

19 Claims, 3 Drawing Sheets

U.S. PATENT DOCUMENTS

2010/0000304 A1* 1/2010 Kim et al. .................... 73/64.56

FOREIGN PATENT DOCUMENTS

| JP | 2003-130846 | 5/2003 |
| JP | 2003-532116 | 10/2003 |
| JP | 2005-345243 | 12/2005 |
| JP | 2006-112789 | 4/2006 |
| WO | WO 01/84142 A1 | 11/2001 |

OTHER PUBLICATIONS

Buzzeo, Marisa C. et al., "Non-Haloaluminate Room-Temperature Ionic Liquids in Electrochemistry-A Review", Chemphyschem, vol. 5, No. 8, pp. 1106-1120, XP-002399493, (2004).

Liu, Jing-fu et al., "Ionic liquid-based liquid-phase microextraction, a new sample enrichment procedure for liquid chromatography", Jounal of Chromatography A, Elsevier, vol. 1026, No. 1-2, pp. 143-147, XP 004482722, (2004).

Visser, Ann E. et al., "Task-specific ionic liquids for the extraction of metal ions from aqueous solutions", Chem. Commun., No. 1, XP-002419263, pp. 135-136, (2001).

Dubois, Philippe et al., "Ionic Liquid Droplet as e-Microreactor", Anal. Chem., vol. 78, No. 14, pp. 4909-4917, XP 002419264, (2006).

Masami Kumano, et al., "Test for recovering heavy metal ions using ionic liquid as a green solvent", Summary of 66$^{th}$ Meeting of the Japan Society for Analytical Chemistry, Apr. 30, 2005, p. 85 (with partial English translation).

* cited by examiner

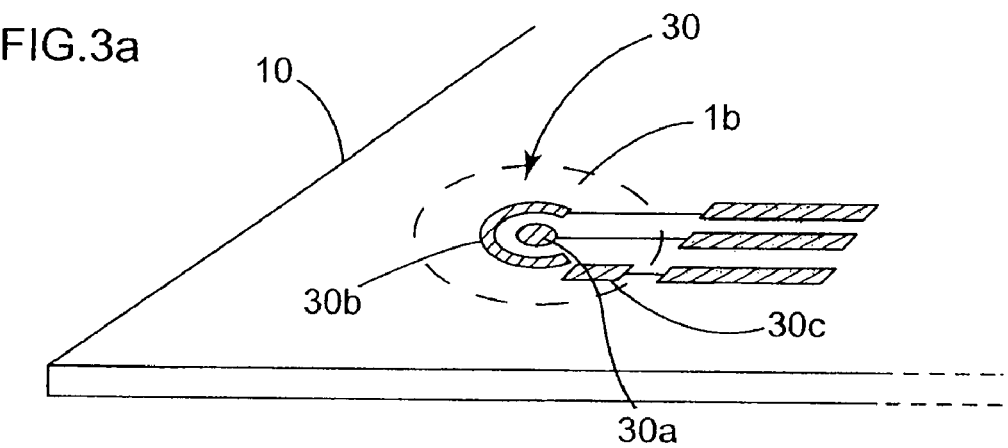
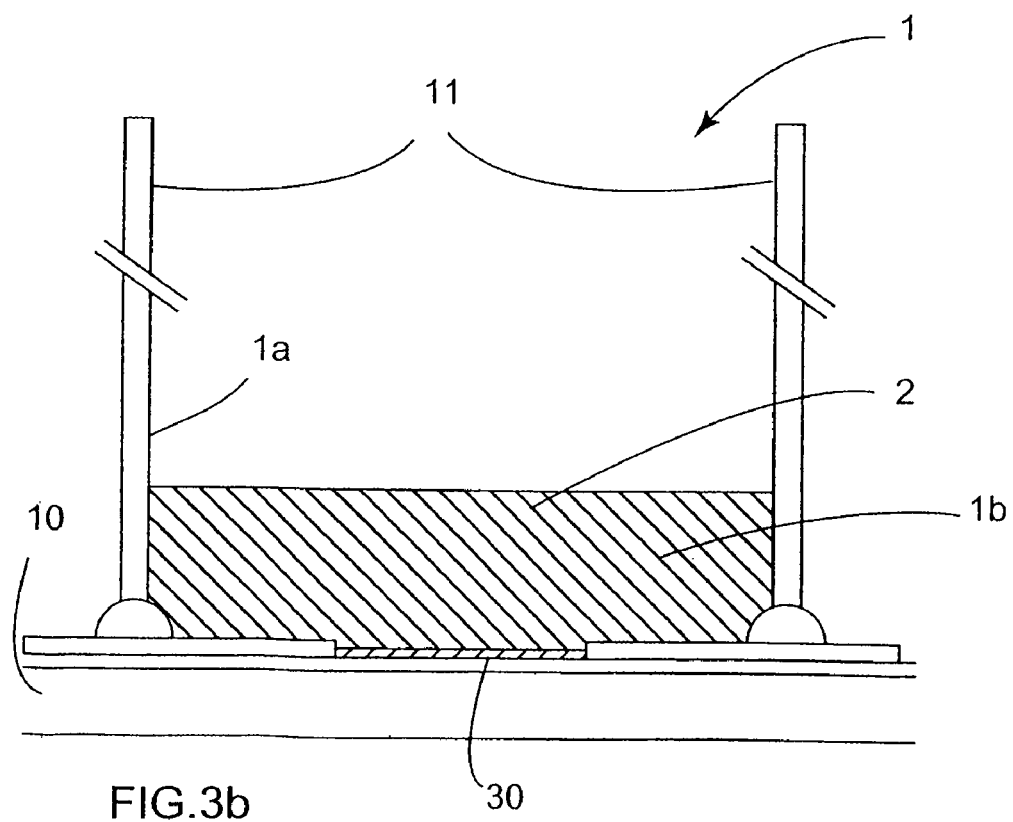

METHOD, DEVICE AND SYSTEM FOR THE MICROANALYSIS OF IONS

The invention relates to a method, a device, and a system for microanalyzing ions. Such a method, device, and system enables ions in solution, e.g. metallic ions in water, to be detected and/or assayed.

It is necessary to assay ions of heavy metals (Ni, Cr, Pb, etc.) in water for health and environmental reasons. Of the 41 elements that comply with this definition, 21 are toxic for man and the environment. Nevertheless, it can be very difficult to detect and/or assay these elements directly in water because they are often present in traces only and because of the limitations of present techniques in terms of sensitivity. Thus, in order to facilitate analysis thereof, it is often necessary to perform a stage of extracting these species into organic solvents of smaller volume, in order to concentrate them. These metals are generally extracted by using complexing or chelating molecules in solution in said solvents.

It is advantageous for ion extraction and analysis to be performed on samples of small volume, typically smaller than one milliliter, specifically in order to reduce the quantity of solvent that is needed. In particular, it is desired to be able to perform these operations on a microanalysis device, also known as a "lab on a chip". The article "Continuous-flow chemical processing on a microchip by combining microunit operations and a multiphase flow network" by Manabu Tokeshi et al. in Anal. Chem. 2002, 74, 1565-1571 describes a microfluidic system enabling Co(II) ions to be extracted and analyzed by complexing in a microfluidic device. The solvent used for extraction is m-xylene and the complexing agent is 2-nitroso-1-naphthol. With such a solvent, extraction is not thermodynamically enhanced, so its efficiency is low. In addition, the volatility of the solvent does not enable small volumes thereof to be used without also using a covering, thereby making the analysis device more complex and constituting an obstacle to easy implementation in parallel on a large number of samples. Such problems are to be encountered with most of the usual solvents.

Room temperature ionic liquids (referred to below as ionic liquids) are known solvents that present advantageous properties, in particular in terms of negligible vapor pressure and the ability to dissolve most organic or inorganic molecules. Depending on the anion or the cation being used, ionic liquids can be miscible or immiscible with water.

The following articles demonstrate the possibility of using ionic liquids as solvents for extracting metallic ions by means of crown ethers, with partition coefficients that are greater than when using a conventional solvent (a "volatile organic solvent"):

Sheng Dai et al. "Solvent extraction of strontium nitrate by a crown ether using room-temperature ionic liquids", J. Chem. Soc. Dalton Trans. 1999, 1202-1202; and Huimin Luo et al. "Extraction of cesium ions from aqueous solutions using Calix[4]arene-bis(tert-octylbenzo-crown-6) in ionic liquids", Anal. Chem. 2004, 76, 3078-3083.

The techniques described in those articles nevertheless require relatively large quantities of ionic liquid to be used (several milliliters), and even larger quantities of the aqueous solution that is to be analyzed. In addition, using those techniques, the analysis is performed remotely from the point of extraction, which makes it necessary to perform complex manipulations.

The article by Jing-fu Lui et al. "Ionic liquid-based liquid-phase microextraction, a new sample enrichment procedure for liquid chromatography", in Journal of Chromatography A, 1026 (2004), 143-147 describes a technique for extracting metallic ions that uses a small volume (microliters) of an ionic liquid suspended in the form of a droplet in a receptacle containing an aqueous solution that is to be analyzed, the ions then being assayed by chromatography. That technique is complex and requires a large number of manipulations that are lengthy and tricky, and difficult to automate.

An object of the invention is to provide a method, a device, and a system for microanalyzing ions that does not present at least some of the above-mentioned drawbacks, or that presents them, but in attenuated form.

In accordance with the invention, ions are extracted and analyzed in a single cavity containing a small volume of an ionic liquid together with ion analyzer means in contact with the ionic liquid; the volume of ionic liquid must be smaller than the inside volume of the cavity, so as to enable a volume of the solution that is to be analyzed to be introduced into the cavity. In the meaning of the invention, the term "cavity" can be understood as including, for example, a channel or a furrow in a fluidic chip, or else a well.

Because of the very low vapor pressure of ionic liquids, which practically do not evaporate, the cavity containing the ionic liquid constitutes a device that can be kept ready for use over a long period, and without it being necessary to provide a covering.

Since the operations of extracting and analyzing ions are performed within a single cavity, a microanalysis method of the invention does not require tricky manipulations and it can be implemented simply, and to a large extent automatically. A plurality of analyses can be carried out in parallel using a microanalysis system constituted by a plurality of devices of the invention, e.g. in order to detect and/or assay ions of the same type in a plurality of different solutions, or else to detect a plurality of types of ion in a single solution.

Furthermore, the good electrical conductivity of ionic liquids makes it possible to use electrochemical techniques to assay the extracted ions, thereby enabling the structure of the device of the invention and its method of use to be further simplified.

The term "analysis" is used to mean not only quantitative analysis or assaying, but also mere detection of ions extracted by the ionic liquid.

More precisely, the invention provides a method of microanalyzing ions, the method being characterized in that it comprises the following steps:

placing in a cavity having an internal volume, a volume of an ionic liquid that is smaller than said internal volume;

placing in said cavity a solution containing said ions that are to be analyzed, the solvent of the solution and the ionic liquid being selected so as to be immiscible and so as to enable ions to be transferred from said solution to said ionic liquid; and detecting the presence of said ions in said ionic liquid with analyzer means for analyzing at least one type of said ions in solution in said ionic liquid, in the free state or in the complexed state, said analyzer means being placed in contact with said ionic liquid.

In particular implementations of the method of the invention;

The method may also include a step of stirring said ionic liquid and said solution in such a manner as to facilitate said transfer of ions.

Said solution may contain the ions to be analyzed is an aqueous solution.

Said ions may be metallic ions.

Said step that consists in detecting the presence of said ions in said ionic liquid with said analyzer means may comprise quantitative measurement of the concentration of said ions.

Said ionic liquid may contain in solution at least one molecule having a complexing function for said type of ions to be extracted and analyzed.

The ionic liquid may be mixed with a task-specific ionic liquid having at least one anion or cation that carries a complexing function for said type of ions to be extracted and analyzed.

Said complexing function may be a selective function enabling only a single type of ion to be complexed.

Said ionic liquid or said molecule having a complexing function may include a probe function having at least one detectable physical or chemical property that varies in response to the complexing of the ions to be analyzed.

Said volume of ionic liquid may be less that half, preferably less than one-tenth, and more preferably less than one-hundredth of the volume of the solution containing the ions to be analyzed.

The internal volume of said cavity may be less than 1 milliliter (mL), and preferably less than 500 microliter (μL).

Said volume of ionic liquid may be less than 10 μL, and preferably of the order of 1 μL or less.

Said ionic liquid may present density greater than the density of said solution.

Said cavity may present a bottom and at least one side wall, said volume of ionic liquid being just sufficient to cover said bottom completely. Alternatively, the ionic liquid may be present in even smaller quantity, so as to form a drop on said bottom, in contact with said analyzer means.

Said analyzer means for analyzing at least one type of ion in solution in said ionic liquid may comprise electrochemical analyzer means having at least two and preferably three electrodes in contact with said volume of ionic liquid, said step that consists in detecting the presence of said ions in said ionic liquid with said analyzer means being performed by using an electrochemical technique, in particular by differential pulse volt-amp measurement or by cyclical volt-amp measurement.

Alternatively, said analyzer means for at least one type of ion in solution in said ionic liquid may be optical analyzer means using spectrophotometry or luminescence, said step that consists in detecting the presence of said ions in said ionic liquid with said analyzer means being performed by means of an optical technique.

The invention also provides a device for implementing such a method of microanalyzing ions, the device comprising:

a cavity having an internal volume;

a volume of an ionic liquid placed inside said cavity, said volume of ionic liquid being less than the inside volume of said cavity; and analyzer means for analyzing at least one type of ion in solution in said ionic liquid in the free or the complexed state, said analyzer means being disposed inside said cavity in contact with said volume of ionic liquid.

In particular embodiments of the device of the invention:

Said cavity may present a bottom constituted by an integrated circuit substrate on which there are formed at least two and preferably at least three electrodes in contact with said volume of ionic liquid and constituting means for electrochemically analyzing at least one type of ion in solution in said ionic liquid.

Said cavity may present a side wall formed by a well in a well plate fastened in leaktight manner to said integrated circuit substrate.

The invention also provides a system for microanalyzing ions, the system comprising a plurality of such devices, each device containing an ionic liquid for selectively extracting ions of different types.

The invention also provides a system for microanalyzing ions, the system comprising a plurality of such devices, each containing an ionic liquid for selectively extracting ions of a single type.

Other characteristics, details, and advantages of the invention appear on reading the following description made with reference to the accompanying drawings given by way of example and in which, respectively:

FIGS. 3a and 3b show a microanalysis device in a first particular embodiment of the invention;

Figure 1:
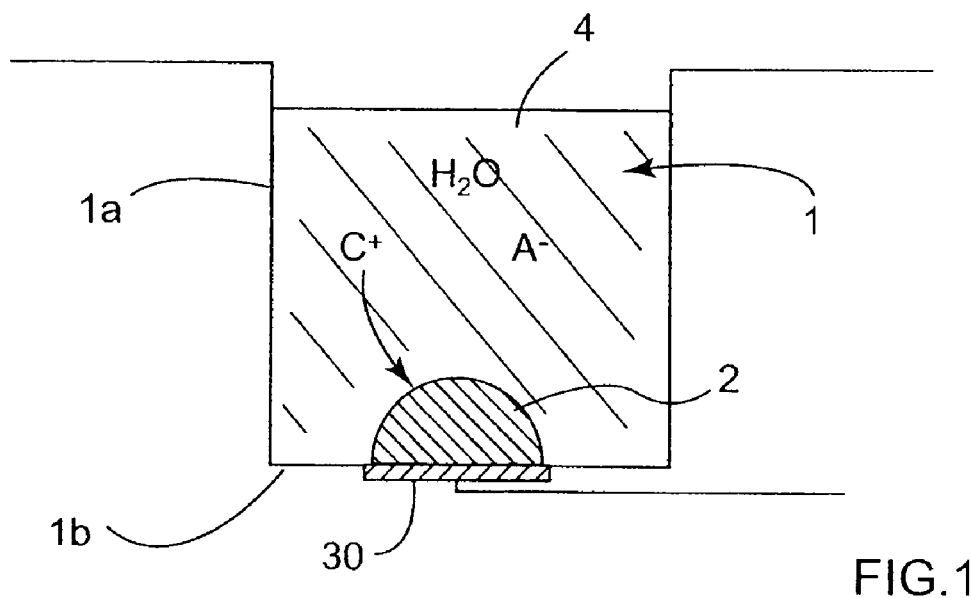
FIG. 1 is a schematic diagram of a device of the invention.

A device of the invention is constituted by a cavity 1 generally having a side wall 1a and a bottom 1b, having an internal volume and containing a predefined volume, less than said internal volume, of an ionic liquid. In FIG. 1, the ionic liquid 2 forms a drop deposited on the bottom 1b of the cavity 1. Inside the cavity 1, in contact with the drop of ionic liquid 2, there are ion analyzer means 3 (for detecting and/or assaying ions). In the example of FIG. 1, the means 3 are placed on the bottom 1b of the cavity 1 and they are completely covered by the drop of ionic liquid 2; in a variant, and as shown in FIG. 3, the means may be arranged in the side wall 1a of said cavity. The cavity 1 generally presents an internal volume of less than 1 mL, and typically of a few hundreds of μL, e.g. 500 μL. The volume of the drop of ionic liquid 2 is significantly smaller, e.g. a few μL or even about 1 μL. The term "ionic liquid" is used to mean a salt or a mixture of salts, generally organic salts, that is liquid at a temperature lying in the range −100° C. to +250° C., and more particularly at a temperature of less than 100° C., or even at room temperature (such salts are known by the acronym RTIL which stands for room-temperature ionic liquids).

The portion of the internal volume of the cavity 1 that is not occupied by the drop of ionic liquid 2 can be filled with a solution for analysis 4, e.g. an aqueous solution, which solution is not considered as forming part of the device. Since the ionic liquid 2 is heavier than water (generally presenting density of about 1.3 grams per cubic centimeter (g/cm$^3$) to 1.4 g/cm$^3$) and since it is immiscible therewith, it maintains the form of a drop deposited on the bottom 1b of the cavity and it remains in contact with the ion analyzer means. In a variant, in order to ensure good contact between the ionic liquid 2 and the analyzer means 3 located on the bottom of the cavity 1 while enabling the ions for analysis to be at high concentration, it can be advantageous to use a quantity of said ionic liquid 2 that is just sufficient for completely covering the bottom 1b of said cavity, instead of forming a drop as shown in FIG. 1.

Initially, the aqueous solution 4 contains metallic cations $C^+$ and anions $A^-$; the ionic liquid 2 presents high affinity with metallic cations and therefore tends to extract them; the extraction of ions by the ionic liquid is itself facilitated thermodynamically, but it can be made even faster and more effective by complexing reactions, as described in detail below. Since the volume of the ionic liquid 2 is less than or equal to the volume of the aqueous solution 4, extraction can have the effect of concentrating the metallic cations $C^+$, thereby enabling them to be analyzed by the means 3 even when they are present in the state of traces only in said solution.

In order to extract metallic cations $C^+$, it can be understood that the partition coefficient D, defined as being the equilibrium ratio between the concentrations of ions in the ionic liquid and in water, needs to be sufficiently high, e.g. of the order of $10^3$. In an advantageous implementation of the invention, extraction is assisted by a complexing reaction, thereby enabling partition coefficients to be achieved that sometimes exceed $10^4$.

A first way of implementing the invention comprises using so-called "matrix" ionic liquids that are chemically inert and that act solely as solvents in which there are dissolved molecules that possess a complexing function. Examples of matrix ionic liquids suitable for implementing the invention are the following (this list is not exhaustive):

1-butyl-3-methylimidazolium hexafluorophosphate (BmimPF6);
1-butyl-3-methylimidazolium bis (trifluoromethylsulfonyl) imide (BmimNTF2);
1-ethyl-3-methylimidazolium hexafluorophosphate (EmimPF6);
1-ethyl-3-methylimidazolium tris (pentafluoroethyl)trifluorophosphate (EMIMFAP);
1-butyl-1-methylimidazolium tris (pentafluoroethyl)trifluorophosphate (BMIMFAP);
butyltrimethylammonium bis (trifluoromethylsulfonyl)imide (BtmaNTF2);
1-butyl-1-methyl-pyrrolidinium bis(tri-fluoromethylsulfonyl)imide (BMPTF2); and
other salts of ammonium, phosphonium, imidazolium, pyridinium, or guanidinium.

The complexing molecule may be selected from the non-exhaustive list comprising: crown ethers; cryptands; podands; cyclophanes; calixarenes; carboxylic acids; thioureas; urea; thioethers; boron derivatives; lariates; rotaxanes; azines; ethylene diamine tetracetic acid (ETDA); and enzymes.

Another possibility consists in mixing the matrix ionic liquid with a task-specific ionic liquid, which task relates to the anion, to the cation, or to both ions constituting a complexing function selected from the above list. The use of a task-specific ionic liquid or of an onium salt in the pure state is impeded by the fact that these substances are not generally liquid at room temperature.

Regardless of whether it is carried by a molecule of the solute or by one of the ions constituting a task-specific ionic liquid mixed with the matrix ionic liquid, the complexing function is advantageously specific, i.e. it enables a single type of ion to be extracted in preferential manner.

In particular implementations of the invention, the ionic liquid 2 includes a "probe" function that is generally grafted to the complexing molecule or function, which "probe" function has at least one detectable chemical or physical property (a property that is optical, electrochemical, etc.) that is influenced by ions complexing. The "probe" thus enables said ions to be detected indirectly. In other implementations of the invention, the complexing function also provides a probe function.

Non-exhaustive examples of probes are the following:
ferrocene, nitrophenyl, the quionone-hydroquinone and pyrene pair, for electrochemical detection;
pyrene or any fluorophore capable of presenting a response that differs before and after complexing of an ion, for optical detection; and
enzymes, acting both as selective complexing molecules and as biological probes.

When the ionic species presents a suitable "signature", it is also possible to detect it directly, without having recourse to a probe, in particular by electrochemical techniques. The signature that enables detection to take place may be a redox response: this applies for example to zinc, iron, chlorine, lead, cadmium, etc.

Consideration is given herein to extracting and detecting and/or measuring cations $C^+$. Nevertheless, the invention also makes it possible to extract and analyze anions $A^-$ from the solution, or indeed ions of both types; this can be done merely by using a suitable combination of ionic liquid 2 and of analyzer means 3. Furthermore, the cations $C^+$ are not necessarily metallic: they may for example be cations of phosphonium or of ammonium.

The table below gives specific examples of ionic liquids that enable ionic species to be detected indirectly, electrically, or optically. The first column of the table contains ions to be detected; the second column contains matrix ionic liquids that are immiscible with water; the third column contains task-specific ionic liquids carrying a probe function and capable of being mixed with said matrix ionic liquids in order to extract and detect the ions of the first column; the fourth column contains complexing molecules also carrying a probe function and capable of being dissolved in the matrix ionic liquids to extract and detect said ions; and finally the fifth column indicates the detection method that can be used: electrochemical (E), or optical (O).

| Ion to be detected | Matrix ionic liquid | Specific-task ionic liquid with probe function | Complexing molecule with probe function | Detection |
|---|---|---|---|---|
| $Ca^{2+}$ | Bmim PF6 | 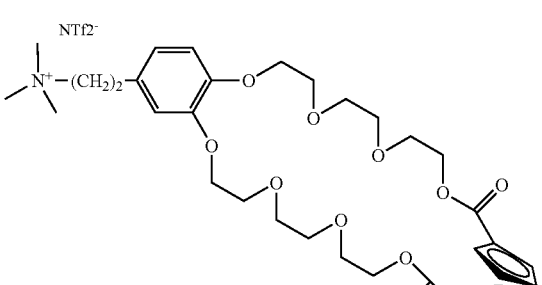 NTf2$^-$ | 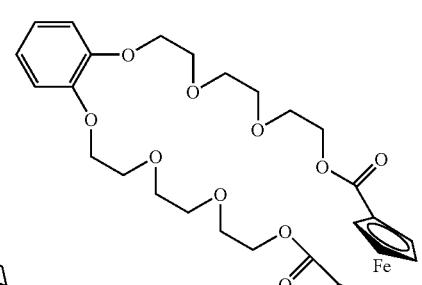 | E |

-continued

| Ion to be detected | Matrix ionic liquid | Specific-task ionic liquid with probe function | Complexing molecule with probe function | Detection |
|---|---|---|---|---|
| $Hg^{2+}$ | Bmim PF6 | ![structure] | ![structure] | E |
| $Hg^{2+}$ | Bmim PF6 | — | ![structure] | E |
| $Hg^{2+}$ | Bmim PF6 | ![structure] | — | E |
| $Hg^{2+}$ | BMPN TF2 | | ![structure] | O |
| $K^+$ | BMPF AP | — | ![structure] $C_{29}H_{35}FeO_2$ Mol Wt.: 568.44 | E |

-continued

| Ion to be detected | Matrix ionic liquid | Specific-task ionic liquid with probe function | Complexing molecule with probe function | Detection |
|---|---|---|---|---|
| F⁻ | BMPF AP | — | 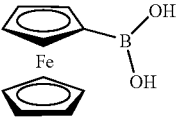 | E |

The various steps of an ion microanalysis method of the invention are shown in FIGS. 2A to 2E.

The first step (FIG. 2A) consists in providing a device of the invention that does not yet contain the solution 4 to be analyzed.

The second step (FIG. 2B) consists in introducing, e.g. by means of a pipette 5, a solution 4 to be analyzed in the cavity 1 of the device of the invention.

In order to accelerate extraction, it is advantageous to maximize the contact area between the solution 4 to be analyzed and the ionic liquid 2. To do this, it is appropriate to provide a third step (FIG. 2C) of stirring so as to form an emulsion 6 of said ionic liquid 2 in the aqueous solution 4 in which it is immiscible. By way of example, the stirring may be performed by placing the device inside a thermomixer. The complexing and the extraction of the ions takes place mainly during this stirring stage.

Figures 2A, 2B, 2C:
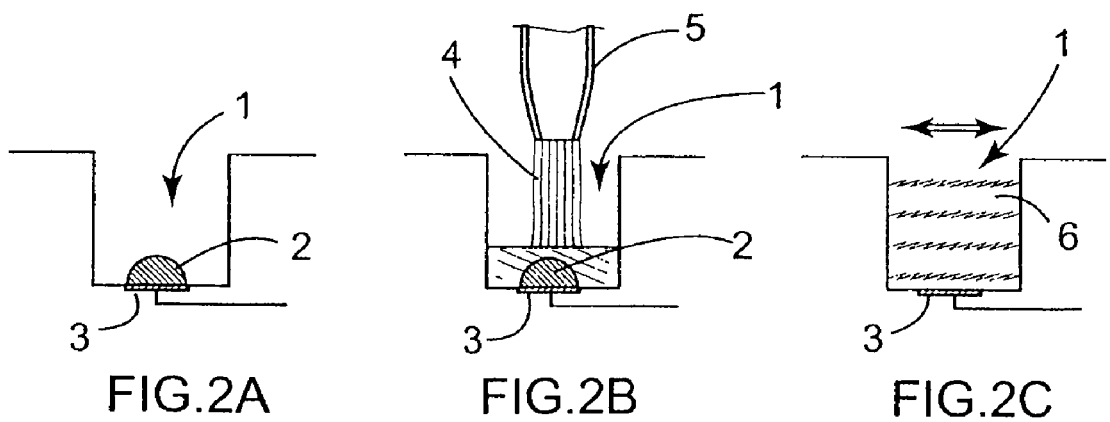
FIGS. 2A to 2E show the various steps of a microanalysis method of the invention.
Figures 2D, 2E:
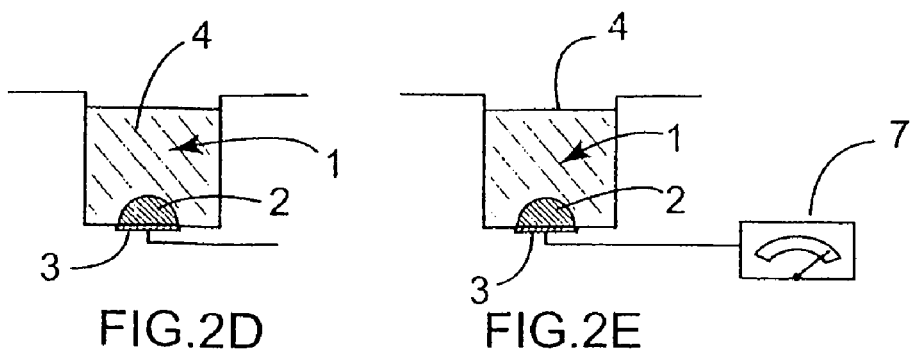

The difference in density between the ionic liquid 2 and the aqueous solution 4 causes these two immiscible phases to separate by settling (FIG. 2D). At this point, practically all of the metallic cations C⁺ have passed from the solution into the ionic liquid 2, in the form of complexes if a complexing agent is present.

Finally, the ion analyzer means 3 in contact with the ionic liquid 2 serves to detect and preferably to assay, the ions extracted by said ionic liquid. A measuring instrument 7 serves to display the results of this detection or assay step.

A detailed implementation of a device and a method of the invention are described below with reference to FIGS. 3a and 3b.

The bottom 1b of a cavity 1 of the invention is made using microelectronic techniques of the kind used for fabricating integrated circuits, starting from an n-doped silicon substrate 10 with a diameter of 100 millimeters (mm) and covered in a 500 nanometer (nm) thick layer of SiO₂ obtained by oxidation at 1050° C. under a stream of steam. A 500 nm thick layer of platinum Pt is deposited on the substrate by sputtering. Thereafter, a layer of photosensitive resin is deposited by centrifuging on the layer of Pt. The photosensitive resin layer is exposed through a photolithographic mask to define a pattern 30 of microelectrodes and of conductor tracks constituting means for analyzing ions electrochemically. In particular, the pattern has a circular working electrode 30a with a diameter of 300 micrometers (μm), a ring-shaped counter-electrode 30b with a width of 130 μm and surrounding the working electrode, and a reference electrode 30c of rectangular shape having dimensions of 50 μm×130 μm, with the distance between the electrodes being 70 μm.

After the non-exposed photosensitive resin has been removed, the pattern is etched using an argon ion beam ("Argon Ion Batch Etch System, Veeco Microtech 801"); after which the exposed resin is in turn removed.

An SiO₂ layer with thickness of 500 nm is formed by plasma-enhanced chemical vapor deposition (PECVD) on the surface of the substrate 10 (deposition performed at 300° C. by an "STS Multiplex" machine using a mixture of SiH₄ and of N₂O) and is stoved at 500° C. for 3 hours (h) under a stream of nitrogen.

A second layer of photosensitive resin is deposited on the SiO₂ layer and is exposed in such a manner as to enable said layer of SiO₂ to be opened in register with the electrodes 30a, 30b, and 30c and in register with points providing connection to the conductor tracks.

Opening is performed by etching using a beam of reactive CHF₃/O₂ ions (a "Nextral 100" machine).

The side wall 1a defining the cavity 1 is constituted by a polyethylene tube 11 bonded to the substrate forming the bottom 1b by means of a "Vitralit 7105" adhesive polymerized by ultraviolet (UV) radiation. The total volume of the cavity obtained in this way is 500 μL.

A volume of about 100 μL of [bmin][PF6] containing 2 milligrams per milliliter (mg/mL) of 1,4-bis(ferrocenyl)-2,3-diaza-1,3-butadiene as complexing agent is deposited on the bottom 1b of the cavity, in contact with the electrode system 30. The 1,4-bis(ferrocenyl)-2,3-diaza-1,3-butadiene is synthesized using the method described by Caballero et al. in J. Am. Chem. Soc. 2005, 127 (45) pp. 15666-15667.

An aqueous solution 4 comprising 200 μL of HgCl₂ at 10 millimoles (mM) is introduced into the cavity 1 of the device as made in this way. Extraction is performed at room temperature in a thermomixer at 1500 revolutions per minute (rpm) that is used as a stirring device, for a duration of 10 minutes (min). Thereafter, the electrode system 30 is connected to potentiostat in order to perform electrochemical measurements by differential pulse volt-amp measurement or by cyclical volt-amp measurement. The complexing of the mercury by the azine function induces a modification of the electrochemical response of the ferrocene, acting as an electrochemical probe. The concentration of Hg²⁺ ions in the ionic liquid 2 is associated with the displacement of potentials (ΔE) by means of charts of ΔE=f([ions]), where ΔE is the variant in the redox potential of the probe before and after complexing and [ions] is the concentration of the concentrated ions. These charts depend on the nature of the probe and of the complexed ions. When a direct electrochemical analysis technique (without a probe) is used, it is possible to make use of the Randles-Sevcik equation:

$$i_p = (2.69 \times 10^5)_n{}^{3/2} \times A'D^{1/2} \times C \times v^{1/2}$$

where $i_p$ is the peak current, n is the number of electrons of the redox reaction, A is the area of the surface of the working electrode, C is the concentration of ions in solution to be detected, and v is the scanning speed. Given the ratio between the volumes of ionic liquid 2 and of aqueous solution 4 in the cavity, and assuming that all of the metallic ions have been extracted, it is possible to calculate their starting concentrations in the solution to be analyzed.

Detection and/or assay of metallic ions can be performed using techniques other than electrochemical techniques, generally by using a probe, e.g. by spectrophotometry, by bioluminescence, or by colorimetry. Electrochemical techniques may make use of two electrodes, or preferably of three electrodes.

Figure 4:
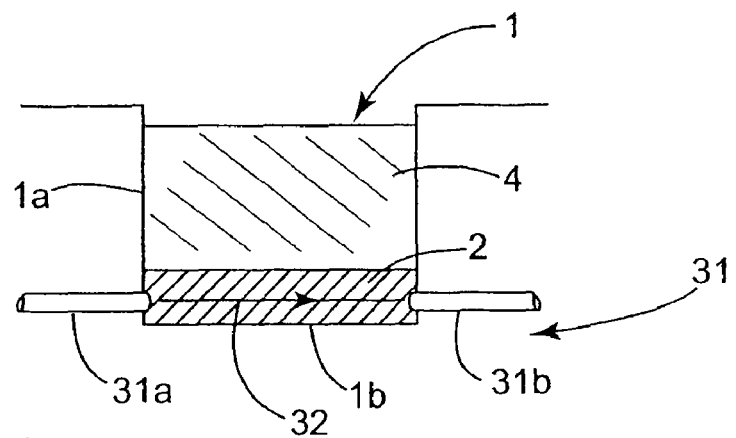
FIG. 4 shows a microanalysis device in a second particular embodiment of the invention.

FIG. 4 shows a device in a second embodiment of the invention, in which the ion analyzer means 31 are constituted by two optical fibers 31a and 31b that penetrate into the cavity 1 through its side wall 1a; the end surfaces of the two optical fibers 30a and 30b face each other, such that a light ray 32 leaving one of the two fibers can penetrate into the other. With the device of FIG. 4, the ionic liquid 1 is not in the form of a drop, but fills the cavity 1 in part, touching its side wall 1a up to a height that is above the height of the end surfaces of the optical fibers 31a and 31b. In operation, a light beam 32 leaves the optical fiber 31a, passes through the ionic liquid 2, and penetrates into the optical fiber 31b that conveys it to a spectrophotometer (not shown). The complexing of metallic ions leads to a modification in the absorption spectrum or the fluorescence spectrum of a probe function for the ionic liquid (e.g. a pyrene-based probe), which modification is revealed by said spectrophotometer, thereby enabling said ions to be detected and assayed.

By way of example, the optical fibers could be replaced by integrated planar waveguides.

Figure 5:
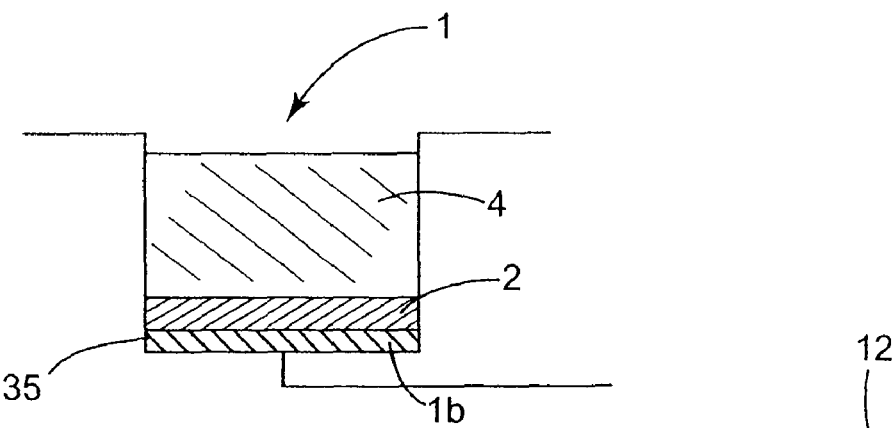
FIG. 5 shows a microanalysis device in a third particular embodiment of the invention.

FIG. 5 shows a device in a third embodiment of the invention, in which the ion analyzer means are constituted by a photodetector 35 extending over all or a significant fraction of the bottom 1b of the cavity 1. As its complexing molecule, the ionic liquid 2 contains an enzyme that operates only in the presence of certain ions and that is stable in the selected ionic liquid. For example, alkaline phosphatase and luciferase operate only in the presence of $Mg^{2+}$ ions and their response is a function of the concentration of these ions. The ionic liquid also contains one or more enzymatic substrates and the product of the enzymatic reaction is luminescent. In the presence of $Mg^{2+}$ ions, the enzyme catalyzes transformation of the substrate(s) into a luminescent product, which then emits photons that are picked up by the photodetector 35. For luciferase, suitable substrates are luciferene and adenosine triphosphate (ATP), and for alkaline phosphatase a derivative of adamantyl 1,2-dioxetane aryl phosphate.

In a variant, the photodetector 35 may be arranged on the side wall 1a of the cavity 1.

The devices shown in FIG. 4 or 5 can be used, for example, to detect mercury ($Hg^{2+}$ ions) optically. To do this, there is placed in the cavity 1 of such a device a volume 2 of about 100 µL of BMPNTF2 containing $5 \times 10^{-4}$ moles (M) of 8-hydroxyquinoline benzoate as the complexing agent and fluorescent probe, together with a volume 4 of 300 µL of a 10 mM aqueous solution of $HgCl_2$. Extraction can be performed at room temperature in a 1500 rpm thermomixer over a duration of 10 min. Thereafter the ionic liquid is illuminated at a wavelength of 365 nm, by means of the optical fiber 31a or by means of a fluorescence lamp placed above the cavity 1. The non-complexed 8-hydroxyquinoline is not excited at this wavelength, whereas after complexing, a band of fluorescence is observed that is centered on 485 nm.

Figure 6:
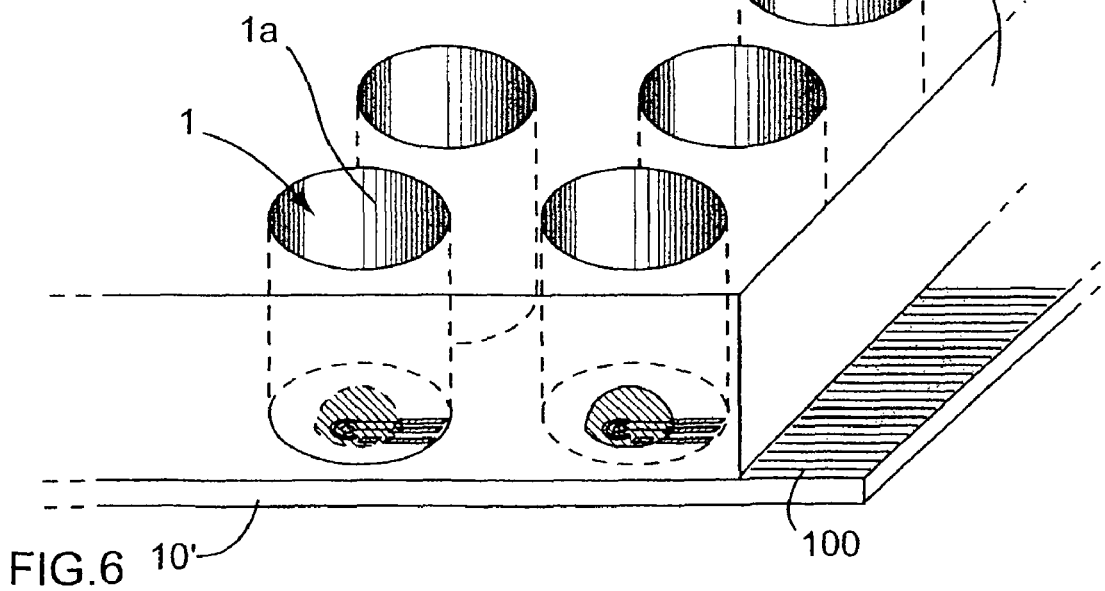
FIG. 6 shows a microanalysis device constituted by a plurality of devices in a fourth particular embodiment of the invention.

Above, consideration is given solely to a device that is isolated. In reality, one of the advantages of the invention lies in the possibility of performing analyses on a plurality of samples in parallel, e.g. for the purpose of identifying and assaying a plurality of ions in a common aqueous solution, or of identifying and assaying the same ions in a plurality of different aqueous solutions. Such parallel analyses can be performed using the system shown in FIG. 6, which is constituted by an arrangement of a plurality of devices of the invention. The system comprises a substrate 10' on which a plurality of electrode systems of the type described with reference to FIGS. 3a and 3b have been made, being arranged in a regular grid; the substrate 10' constitutes the bottom of all of the cavities in the system. The side walls 1a are embodied as openings arranged in the same grid pattern as the electrodes and made through a plate 12 (a well plate) that is typically made of plastics material and that is stuck to the substrate 10'. The substrate 10' projects a little beyond the plate 12 so as to expose the electrical contacts 100 that enable connections to be made to the electrodes of the measurement devices. In this way, an electrochemical "chip" is obtained combining in a very small volume tens or even hundreds of devices of the invention. By way of example, each well plate typically presents 96 or 384 openings.

The "chip" as made in this way is made suitable for a particular use by introducing into each cavity a predetermined quantity of a matrix ionic liquid containing a task-specific ionic liquid or a complexing molecule. For example, if it is desired to detect and/or assay a plurality of types of ion in a sample of a single solution (e.g. all ions of toxic heavy metals in a sample of potable water), then each cavity contains a different ionic liquid, or the same ionic liquid with a different complexing function or molecule. In contrast, if it is desired to perform the same analysis on a plurality of different samples (e.g. to measure the $Hg^{2+}$ ion content of samples of water taken from different rivers, or from different sites along a single river), then the same ionic liquid and the same complexing molecule are introduced into each of the cavities.

It will be understood that the various analysis can be carried out in parallel using the method shown in FIGS. 2A to 2E, thus requiring no more manipulations than are required for a single analysis.

The invention is described above with reference to certain particular implementations, but numerous variants are possible.

The ions being detected and assayed may be ions other than heavy metal ions. For example, the invention can be used to assay ions of alkali and alkaline earth metals in biological samples in order to carry out medical analyses, to assay ammonium cations, halide anions, etc.

Various ionic liquids and complexing functions or molecules are mentioned in the description, but solely as non-limiting examples. The same applies to the probes and to the ion analyzer means.

It is also possible to perform analyses in accordance with the invention using solutions based on solvents other than water: it suffices for the ionic liquid to be selected in such a manner as to be immiscible with said solvent and to be effective in extracting the ions that are to be assayed. The difference in density between the ionic liquid and the solution to be analyzed is also important in order to ensure contact between said ionic liquid and the ion analyzer means. Although the only configuration considered in the example is that of the ionic liquid being denser than the solution, the converse is likewise possible; under such circumstances, the analyzer means must be arranged in the top portion of the cavity.

In the embodiment described in detail with reference to FIGS. 3a and 3b, the content of the cavity is stirred with the help of a "macroscopic" thermomixer. Other stirring techniques can also be considered. In particular, it is known to stir microliter-scale quantities of liquid on the surface of a microfluidic chip by using surface acoustic waves. A device or system of the invention may have stirring means incorporated therein, e.g. based on the surface acoustic wave techniques, thereby eliminating the need to use "macroscopic" stirring means.

A device or system of the invention might constitute merely an element of some larger microanalysis system, e.g. a microfluidic system having means for moving small quantities of liquid on a chip.

The invention claimed is:

1. A method of microanalyzing ions, which comprises:
   placing in a cavity having an internal volume, a volume of an ionic liquid that is smaller than said internal volume;
   placing in said cavity a solution containing said ions that are to be analyzed, a solvent of the solution and the ionic liquid being selected so as to be immiscible and so as to enable said ions to be transferred from said solution to said ionic liquid; and
   detecting a presence of said ions in said ionic liquid with an analyzer that analyzes at least one of cations or anions of said ions in solution in said ionic liquid, in a free state or in a complexed state, said analyzer being in contact with said ionic liquid.

2. The method according to claim 1, which further comprises stirring said ionic liquid and said solution in such a manner as to facilitate transfer of said ions from said solution to said ionic liquid.

3. The method according to claim 1, wherein said solution containing the ions to be analyzed is an aqueous solution.

4. The method according to claim 1, wherein said ions are metallic ions.

5. The method according to claim 1, wherein the presence of said ions in said ionic liquid is detected with said analyzer by quantitative measurement of the concentration of said ions.

6. The method according to claim 1, wherein said ionic liquid contains in solution at least one molecule having a complexing function for said ions which are to be extracted and analyzed.

7. The method according to claim 1, wherein the ionic liquid is mixed with a task-specific ionic liquid having at least one anion or cation that carries a complexing function for said ions which are to be extracted and analyzed.

8. The method according to claim 6, wherein said complexing function is a selective function enabling only a cation or only an anion to be complexed.

9. The method according to claim 6, wherein said ionic liquid or said at least one molecule having a complexing function that comprises a probe function having at least one detectable physical or chemical property that varies in response to the complexing of the ions to be analyzed.

10. A method according to claim 1, wherein said volume of ionic liquid is less than the volume of the solution containing the ions to be analyzed, so as to enable said ions to be concentrated when extracted.

11. The method according to claim 10, wherein said volume of ionic liquid is less than one-tenth of the volume of the solution containing the ions to be analyzed.

12. The method according to claim 1, wherein the internal volume of said cavity is less than 1 mL.

13. The method according to claim 1, wherein said volume of ionic liquid is less than 10 µL.

14. The method according to claim 1, wherein said ionic liquid presents a density greater than a density of said solution.

15. The method according to claim 14, wherein said cavity presents a bottom and at least one side wall, and wherein said volume of ionic liquid forms a drop on said bottom.

16. The method according to claim 14, wherein said cavity presents a bottom and at least one side wall, and wherein said volume of ionic liquid is just sufficient to completely cover said bottom.

17. The method according to claim 1, wherein said analyzer comprises an electrochemical analyzer having at least two electrodes in contact with said volume of ionic liquid, and wherein the presence of said ions in said ionic liquid is detected by an electrochemical technique with said analyzer.

18. The method according to claim 17, wherein said electrochemical technique is by differential pulse volt-amp measurement or by cyclical volt-amp measurement.

19. The method according to claim 1, wherein said analyzer is a spectrophotometric or luminescent optical analyzer and wherein the presence of said ions in said ionic liquid with said analyzer is detected by an optical technique.

* * * * *

UNITED STATES PATENT AND TRADEMARK OFFICE
CERTIFICATE OF CORRECTION

| | | |
|---|---|---|
| PATENT NO. | : 8,298,399 B2 | Page 1 of 1 |
| APPLICATION NO. | : 12/302947 | |
| DATED | : October 30, 2012 | |
| INVENTOR(S) | : Gilles Marchand | |

It is certified that error appears in the above-identified patent and that said Letters Patent is hereby corrected as shown below:

On the title page, Item (86), the Application Filing Date is incorrect. Item (86) should read:

-- (86)  PCT No.:     PCT/FR2007/000874

§ 371 (c)(1),
(2), (4) Date:   Dec. 15, 2008 --

Signed and Sealed this
Fifteenth Day of January, 2013

David J. Kappos
*Director of the United States Patent and Trademark Office*